(12) United States Patent
Trieu (10) Patent No.: US 7,985,246 B2
(45) Date of Patent: Jul. 26, 2011

(54) METHODS AND INSTRUMENTS FOR DELIVERING INTERSPINOUS PROCESS SPACERS

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 907 days.

(21) Appl. No.: 11/394,965

(22) Filed: Mar. 31, 2006

(65) Prior Publication Data
US 2007/0233076 A1   Oct. 4, 2007

(51) Int. Cl.
*A61B 17/88* (2006.01)
*A61B 17/70* (2006.01)
(52) U.S. Cl. .................... 606/279; 606/249
(58) Field of Classification Search .......... 606/53, 606/60–61, 76, 78, 99, 104–105, 198, 246–249, 606/323, 914; 623/17.11–17.15, 17.16
See application file for complete search history.

(56) References Cited

U.S. PATENT DOCUMENTS

| | | | |
|---|---|---|---|
| 2,677,639 A | 3/1952 | Knowles | |
| 2,677,369 A | 5/1954 | Knowles | |
| 3,486,505 A | 12/1969 | Morrison | |
| 3,648,691 A | 3/1972 | Lumb et al. | |
| 4,011,602 A | 3/1977 | Rybicki et al. | |
| 4,257,409 A | 3/1981 | Bacal et al. | |
| 4,369,769 A | 1/1983 | Edwards | |
| 4,554,914 A | 11/1985 | Kapp et al. | |
| 4,573,454 A | 3/1986 | Hoffman | |
| 4,604,995 A | 8/1986 | Stephens et al. | |
| 4,686,970 A | 8/1987 | Dove et al. | |
| 4,827,918 A | 5/1989 | Olerud | |
| 4,997,432 A | 3/1991 | Keller | |
| 5,011,484 A | 4/1991 | Breard | |
| 5,047,055 A | 9/1991 | Bao et al. | |
| 5,092,866 A | 3/1992 | Breard et al. | |
| 5,201,734 A | 4/1993 | Cozad et al. | |
| 5,306,275 A | 4/1994 | Bryan | |

(Continued)

FOREIGN PATENT DOCUMENTS
DE  2821678 A1  11/1979
(Continued)

OTHER PUBLICATIONS

European Patent Office, International Searching Authority, Notification of Transmittal of the International Search Report and the Written Opinion of the International Searching Authority or the Declaration, International Application No. PCT/US2007/064345, Aug. 9, 2007, 13 pages.

(Continued)

*Primary Examiner* — Thomas C Barrett
*Assistant Examiner* — Larry E Waggle, Jr.

(57) ABSTRACT

A method for implanting an interspinous process spacer includes deforming a spacer from an extended configuration to a collapsed configuration. The spacer has a first pair of resiliently deformable arms extending from a central section of the spacer and when the spacer is deformed into the collapsed configuration, the first pair of arms moves toward each other. When in the collapsed configuration, the spacer is advanced into a guide tube such that the first pair of arms is constrained only by the guide tube. The guide tube is positioned proximate a pair of adjacent spinous processes and then the spacer is removed from the guide tube so that the first pair of arms resiliently move away from each other and are disposed on a common lateral side of the spinous processes.

13 Claims, 8 Drawing Sheets

U.S. PATENT DOCUMENTS

| | | |
|---|---|---|
| 5,360,430 A | 11/1994 | Lin |
| 5,366,455 A | 11/1994 | Dove |
| 5,415,661 A | 5/1995 | Holmes |
| 5,437,672 A | 8/1995 | Alleyne |
| 5,454,812 A | 10/1995 | Lin |
| 5,489,307 A | 2/1996 | Kuslich et al. |
| 5,496,318 A | 3/1996 | Howland et al. |
| 5,545,170 A | 8/1996 | Hart |
| 5,599,279 A | 2/1997 | Slotman et al. |
| 5,609,634 A | 3/1997 | Voydeville |
| 5,628,756 A | 5/1997 | Barker, Jr. et al. |
| 5,645,599 A | 7/1997 | Samani |
| 5,674,295 A | 10/1997 | Ray et al. |
| 5,676,702 A | 10/1997 | Ratron |
| 5,690,649 A | 11/1997 | Li |
| 5,702,452 A | 12/1997 | Argenson et al. |
| 5,810,815 A | 9/1998 | Morales |
| 5,836,948 A | 11/1998 | Zucherman et al. |
| 5,860,977 A | 1/1999 | Zucherman et al. |
| 5,876,404 A | 3/1999 | Zucherman et al. |
| 5,976,186 A | 11/1999 | Bao et al. |
| 6,022,376 A | 2/2000 | Assell et al. |
| 6,042,582 A | 3/2000 | Ray |
| 6,048,342 A | 4/2000 | Zucherman et al. |
| 6,068,630 A | 5/2000 | Zucherman et al. |
| 6,074,390 A | 6/2000 | Zucherman et al. |
| 6,083,225 A | 7/2000 | Winslow et al. |
| 6,090,112 A | 7/2000 | Zucherman et al. |
| 6,113,602 A | 9/2000 | Sand |
| 6,132,464 A | 10/2000 | Martin |
| 6,149,652 A | 11/2000 | Zucherman et al. |
| 6,152,926 A | 11/2000 | Zucherman et al. |
| 6,156,038 A | 12/2000 | Zucherman et al. |
| 6,159,212 A | 12/2000 | Schoedinger, III et al. |
| 6,171,339 B1 | 1/2001 | Houfburg et al. |
| 6,174,311 B1 | 1/2001 | Branch et al. |
| 6,183,471 B1 | 2/2001 | Zucherman et al. |
| 6,190,387 B1 * | 2/2001 | Zucherman et al. .......... 606/249 |
| 6,224,607 B1 | 5/2001 | Michelson |
| 6,235,030 B1 | 5/2001 | Zucherman et al. |
| 6,238,397 B1 | 5/2001 | Zucherman et al. |
| 6,241,729 B1 | 6/2001 | Estes et al. |
| 6,261,296 B1 | 7/2001 | Aebi et al. |
| 6,261,586 B1 | 7/2001 | McKay |
| 6,280,444 B1 | 8/2001 | Zucherman et al. |
| 6,293,949 B1 | 9/2001 | Justis et al. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,352,537 B1 | 3/2002 | Strnad |
| 6,364,883 B1 | 4/2002 | Santilli |
| 6,379,355 B1 | 4/2002 | Zucherman et al. |
| 6,402,750 B1 | 6/2002 | Atkinson et al. |
| 6,419,676 B1 * | 7/2002 | Zucherman et al. .......... 606/249 |
| 6,419,677 B2 | 7/2002 | Zucherman et al. |
| 6,440,169 B1 | 8/2002 | Elberg et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,554,833 B2 | 4/2003 | Levy |
| 6,565,570 B2 | 5/2003 | Sterett et al. |
| 6,582,433 B2 | 6/2003 | Yun |
| 6,626,944 B1 * | 9/2003 | Taylor ........................ 623/17.16 |
| 6,645,207 B2 | 11/2003 | Dixon et al. |
| 6,652,533 B2 | 11/2003 | O'Neil |
| 6,676,665 B2 | 1/2004 | Foley et al. |
| 6,695,842 B2 | 2/2004 | Zucherman et al. |
| 6,699,246 B2 | 3/2004 | Zucherman et al. |
| 6,699,247 B2 * | 3/2004 | Zucherman et al. ........ 606/86 A |
| 6,709,435 B2 | 3/2004 | Lin |
| 6,723,126 B1 | 4/2004 | Berry |
| 6,733,534 B2 | 5/2004 | Sherman |
| 6,752,832 B2 | 6/2004 | Neumann |
| 6,761,720 B1 * | 7/2004 | Senegas ........................ 606/249 |
| 6,796,983 B1 | 9/2004 | Zucherman et al. |
| 6,835,205 B2 | 12/2004 | Atkinson et al. |
| 6,946,000 B2 | 9/2005 | Senegas et al. |
| 7,041,136 B2 | 5/2006 | Goble et al. |
| 7,048,736 B2 | 5/2006 | Robinson et al. |
| 7,087,083 B2 | 8/2006 | Pasquet et al. |
| 7,163,558 B2 | 1/2007 | Senegas et al. |
| 7,201,751 B2 | 4/2007 | Zucherman et al. |
| 7,238,204 B2 | 7/2007 | Le Couedic et al. |
| 7,252,673 B2 | 8/2007 | Lim |
| 7,306,628 B2 | 12/2007 | Zucherman et al. |
| 7,377,942 B2 | 5/2008 | Berry |
| 7,442,208 B2 | 10/2008 | Mathieu et al. |
| 7,445,637 B2 | 11/2008 | Taylor |
| 2001/0012938 A1 | 8/2001 | Zucherman et al. |
| 2002/0095154 A1 | 7/2002 | Atkinson et al. |
| 2002/0116000 A1 | 8/2002 | Zucherman et al. |
| 2002/0143331 A1 | 10/2002 | Zucherman et al. |
| 2003/0153915 A1 | 8/2003 | Nekozuka et al. |
| 2004/0059318 A1 | 3/2004 | Zhang et al. |
| 2004/0082954 A1 | 4/2004 | Teitelbaum et al. |
| 2004/0097931 A1 | 5/2004 | Mitchell |
| 2004/0106927 A1 | 6/2004 | Ruffner et al. |
| 2004/0106995 A1 | 6/2004 | Le Couedic et al. |
| 2004/0153071 A1 | 8/2004 | Zucherman et al. |
| 2004/0167520 A1 | 8/2004 | Zucherman et al. |
| 2004/0181282 A1 | 9/2004 | Zucherman et al. |
| 2004/0199255 A1 | 10/2004 | Mathieu et al. |
| 2004/0249388 A1 | 12/2004 | Michelson |
| 2005/0010293 A1 | 1/2005 | Zucherman et al. |
| 2005/0049708 A1 | 3/2005 | Atkinson et al. |
| 2005/0055031 A1 | 3/2005 | Lim |
| 2005/0090824 A1 | 4/2005 | Shluzas et al. |
| 2005/0101955 A1 | 5/2005 | Zucherman et al. |
| 2005/0113842 A1 | 5/2005 | Bertagnoli et al. |
| 2005/0119665 A1 | 6/2005 | Keller |
| 2005/0143738 A1 | 6/2005 | Zucherman et al. |
| 2005/0165398 A1 | 7/2005 | Reiley |
| 2005/0171540 A1 | 8/2005 | Lim et al. |
| 2005/0203512 A1 * | 9/2005 | Hawkins et al. ................ 606/61 |
| 2005/0203624 A1 | 9/2005 | Serhan et al. |
| 2005/0228391 A1 | 10/2005 | Levy et al. |
| 2005/0261768 A1 * | 11/2005 | Trieu ........................ 623/17.11 |
| 2005/0288672 A1 | 12/2005 | Feree |
| 2006/0004447 A1 | 1/2006 | Mastrorio et al. |
| 2006/0015181 A1 | 1/2006 | Elberg |
| 2006/0064165 A1 | 3/2006 | Zucherman et al. |
| 2006/0084983 A1 * | 4/2006 | Kim ............................... 606/61 |
| 2006/0084985 A1 * | 4/2006 | Kim ............................... 606/61 |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0122620 A1 | 6/2006 | Kim |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0235387 A1 * | 10/2006 | Peterman ....................... 606/61 |
| 2006/0235532 A1 | 10/2006 | Meunier et al. |
| 2006/0241613 A1 | 10/2006 | Brueneau et al. |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 * | 11/2006 | Zucherman et al. ............ 606/61 |
| 2006/0293662 A1 | 12/2006 | Boyer, II et al. |
| 2006/0293663 A1 | 12/2006 | Walkenhorst et al. |
| 2007/0043362 A1 | 2/2007 | Malandain et al. |
| 2007/0112354 A1 | 5/2007 | Iwasaki et al. |
| 2007/0161992 A1 * | 7/2007 | Kwak et al. ..................... 606/61 |
| 2007/0162000 A1 | 7/2007 | Perkins |
| 2007/0198091 A1 | 8/2007 | Boyer et al. |
| 2007/0233068 A1 | 10/2007 | Bruneau et al. |

| | | | |
|---|---|---|---|
| 2007/0233081 A1 | 10/2007 | Pasquet et al. | |
| 2007/0233089 A1 | 10/2007 | DiPoto et al. | |
| 2007/0270834 A1 | 11/2007 | Bruneau et al. | |
| 2008/0161818 A1 | 7/2008 | Kloss et al. | |

FOREIGN PATENT DOCUMENTS

| | | |
|---|---|---|
| DE | 4217660 A1 | 12/1993 |
| EP | 0322334 | 6/1989 |
| EP | 0322334 B1 | 2/1992 |
| EP | 1138268 | 10/2001 |
| EP | 1138268 A1 | 10/2001 |
| EP | 1330987 A1 | 7/2003 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 | 5/2002 |
| FR | 2816197 A1 * | 5/2002 |
| JP | 02-224660 | 9/1990 |
| JP | 09-075381 | 3/1997 |
| SU | 988281 | 1/1983 |
| WO | WO 94/26192 | 11/1994 |
| WO | WO 94/26195 | 11/1994 |
| WO | WO 98/20939 | 5/1998 |
| WO | 03/045262 | 6/2003 |
| WO | WO 2004/047691 A1 | 6/2004 |
| WO | 2005/009300 | 2/2005 |
| WO | WO 2005/009300 A1 | 2/2005 |
| WO | WO 2005/009300 A1 * | 2/2005 |
| WO | WO 2005/044118 A1 | 5/2005 |
| WO | WO2005051246 A2 | 6/2005 |
| WO | WO 2005/110258 A1 | 11/2005 |
| WO | WO2005115261 A1 | 12/2005 |
| WO | WO 2006/064356 A1 | 6/2006 |
| WO | WO 2007/034516 A1 | 3/2007 |

OTHER PUBLICATIONS

"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," Spine, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," Spine, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," Spine, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," Spine, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.
Petrini et al., "Stabilizzazione Elastica," Patologia Degenerativa del Rachide Lombare, Oct. 5-6, 2001, Rimini.
Porter, "Spinal Stenosis and Neurogenic Claudication," Spine, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," Spine, 2005, pp. 744-749, vol. 30, No. 7.
Scarfò, "Instability/Stenosis: Holistic Approach for Less Invasive Surgery," date unknown, University of Siena, Siena, Italy.
Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopedique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

VanGilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

Kramer et al., "Intevetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," Spine, 1991, pp. S298-S301, vol. 16, No. 6, Supplement.

\* cited by examiner

METHODS AND INSTRUMENTS FOR DELIVERING INTERSPINOUS PROCESS SPACERS

BACKGROUND

Lumbar spinal stenosis ("LSS", and sometimes called sciatica) is a condition of the spine characterized by a narrowing of the lumbar spinal canal. With spinal stenosis, the spinal canal narrows and pinches the spinal cord and nerves, causing pain in the back and legs. One surgical technique for relieving LSS involves distracting adjacent vertebrae and implanting an interspinous process spacer to maintain the desired separation between the segments. This technique is somewhat less invasive than alternative treatments such as decompressive laminectomy, but may actually provide significant benefits to patients experiencing LSS symptoms. As with other surgeries, one consideration when performing surgery to implant an interspinous spacer is the size of the incision that is required to allow introduction of the device. Interspinous spacers previously known to the art were not easily implanted with minimally invasive surgical techniques. A need exists for instrumentation and methods for implanting an interspinous process spacer using minimally invasive surgical techniques.

SUMMARY

In one embodiment, a system for implanting an interspinous process spacer comprises a deformation instrument adapted to engage a pair of opposing arms of the interspinous process spacer and operable to move the opposing arms relative to one another to deform the interspinous process spacer from an uncollapsed state to a collapsed state. The system further comprises a cannula adapted to receive the collapsed interspinous process spacer from the deformation instrument and direct the interspinous process spacer to an area between a pair of spinous processes.

In another embodiment, a system for minimally invasive implantation of an interspinous process spacer comprises a pair of actuators adapted for insertion between a pair of collapsible arms of the interspinous process spacer and a pivot joint connecting the pair of actuators and adapted to cause the actuators to move apart and to thereby move the collapsible arms from an uncollapsed state to a collapsed state.

In another embodiment, a method comprises selecting an interspinous process spacer having a first pair of opposing arms interconnected by a blocking member. The method further comprises selecting a deformation instrument having a first movable portion and a second movable portion, engaging the first movable portion with one of the opposing arms, and engaging the second movable portion with the other opposing arm. The method further includes moving the first movable portion relative to the second movable portion to move the interspinous process spacer into a collapsed state. The method also includes inserting a first guide tube into a space between a pair of spinous processes and inserting the interspinous process spacer in the collapsed state into the first guide tube.

Additional embodiments are included in the attached drawings and the description provided below.

DETAILED DESCRIPTION

The present disclosure relates generally to vertebral device implantation systems, and more particularly, to systems and procedures for minimally invasive interspinous process spacer implantation. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
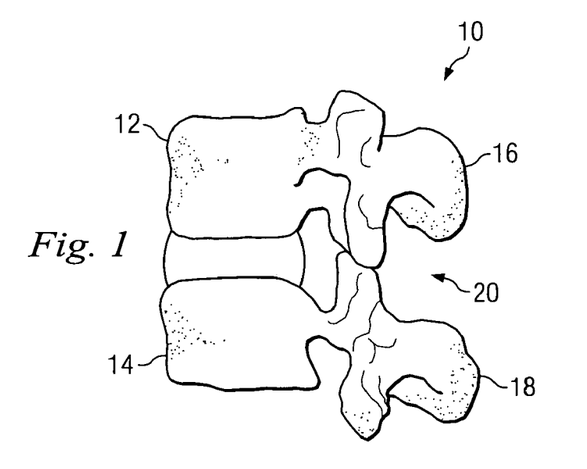
FIG. 1 is a sagittal view of a section of a vertebral column.

Referring first to FIG. 1, the reference numeral 10 refers to a vertebral joint section or a motion segment of a vertebral column. The joint section 10 includes adjacent vertebral bodies 12, 14. The vertebral bodies 12, 14 include spinous processes 16, 18, respectively. An interspinous process space 20 is located between the spinous processes 16, 18.

Figure 2:
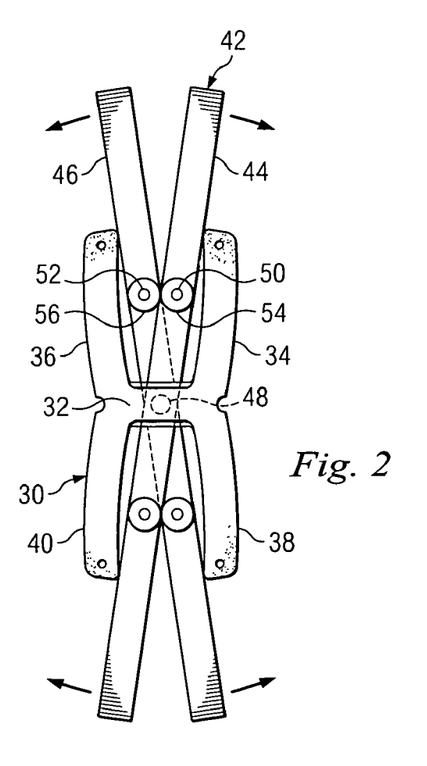
FIG. 2 is an interspinous process spacer engaged with a spacer deformation instrument according to one embodiment of the present disclosure.

Referring now to FIG. 2, an interspinous process spacer 30 is adapted for implantation in the interspinous space 20. The interspinous spacer 30 is designed to maintain a minimal distance between the spinous processes of adjacent vertebrae 12, 14. As such, the spacer 30 has a blocking portion 32 that keeps the vertebrae from coming together. The spacer 30 may be designed to fit snugly around the spinous processes, and thus to avoid being dislodged by movement of the spine. In this embodiment, the spacer 30 achieves a snug fit by including "arms" 34, 36, extending from the blocking portion 32 upward along both sides of the upper spinous process, and "arms" 38, 40 extending from the blocking portion 32 downward along both sides of the lower spinous process. The arms 34, 36, 38, 40 may keep the spacer 30 from moving laterally with respect to the spinous processes. In FIG. 2, spacer 30 is shown in an uncollapsed, generally "H" shaped configuration. The shape as well as the material properties of the spacer may allow it to assume a collapsed configuration which may further allow the spacer to be implanted using a minimally invasive surgical technique.

An interspinous process spacer may be formed from a wide variety of biocompatible materials including those that can undergo reversible elastic deformation. Examples of such materials include elastic or rubbery polymers, hydrogels or other hydrophilic polymers, or composites thereof. Examples of suitable polymers may include silicone, polyurethane, silicone-polyurethane copolymers, polyesters, polyethylenes, polyethyleneterephthaltates, polyaryletherketone (PAEK) polyether block copolymer (PEBAX), ABS (acrylonitrile butadiene styrene), ANS (acrylonitrile styrene), delrin acetal; PVC (polyvinyl chloride), PEN (polyethylene napthalate), PBT (polybutylene terephthalate), polycarbonate, PEI (polyetherimide), PES (polyether sulfone), PET (polyethylene terephthalate), PETG (polyethylene terephthalate glycol), polyamide, aromatic polyamide, polyether, polyester, polymethylmethacrylate, polyurethane copolymer, ethylene vinyl acetate (EVA), ethylene vinyl alcohol, FEP (fluorinated ethylene polymer), PTFE (polytetrafluoroethylen-e), PFA (perfluoro-alkoxyalkane), polypropylene, polyolefin, polysiloxane, liquid crystal polymer, ionomer, poly(ethylene-co-methacrylic) acid, SAN (styrene acrylonitrile), nylon, polyether block amide and thermoplastic elastomer.

The spacer material may be a solid, sheet/film, fiber, mesh and/or braided configurations. The elastomeric material can be formed into a solid one-piece, monoblock unit having the configuration described above. In one alternative, the spacer may be fillable or have otherwise alterable material properties as described more fully below.

Examples of suitable polyurethanes for use in forming a spacer may include thermoplastic polyurethanes, aliphatic polyurethanes, segmented polyurethanes, hydrophilic polyurethanes, polyether-urethane, polycarbonate-urethane and silicone polyetherurethane. Other suitable hydrophilic polymers include polyvinyl alcohol hydrogel, polyacrylamide hydrogel, polyacrylic hydrogel, poly(N-vinyl-2-pyrrolidone hydrogel, polyhydroxyethyl methacrylate hydrogel, and naturally occurring materials such as collagen and polysaccharides, such as hyaluronic acid and cross-linked carboxyl-containing polysaccharides, and combinations thereof.

In other embodiments, the spacer is made of a metal that can undergo reversible elastic deformation, such as shape memory metals or nickel titanium. Further description of interspinous process spacers, of the type shown in FIG. 2, is provided in detail in pending U.S. patent application Ser. No. 10/851,889, entitled "Interspinous Spacer" which is incorporated herein by reference.

FIG. 2 also depicts an interspinous process spacer deformation instrument 42. The instrument 42 includes supports 44, 46 pivotally connected by pivot mechanism 48 and arranged in an "X" shaped configuration. The pivot mechanism 48 may allow the supports 44, 46 to pivotally move relative to each other in the directions shown in FIG. 2. The movement of the pivot mechanism 48 may be controlled or biased by a mechanical spring mechanism, a ratchet mechanism, a shape memory material, or other bias or control mechanisms known in the art. The supports 44, 46 include projections 50, 52, respectively which, as shown in FIG. 2, may be configured to extend between arms 44, 46 of the spacer 30. The projections 50, 52 may be fitted with rollers 54, 56, respectively. The opposite side of the supports 44, 46 may also be fitted with corresponding projections and rollers to fit between arms 38, 40 of the spacer 30.

Figure 3:
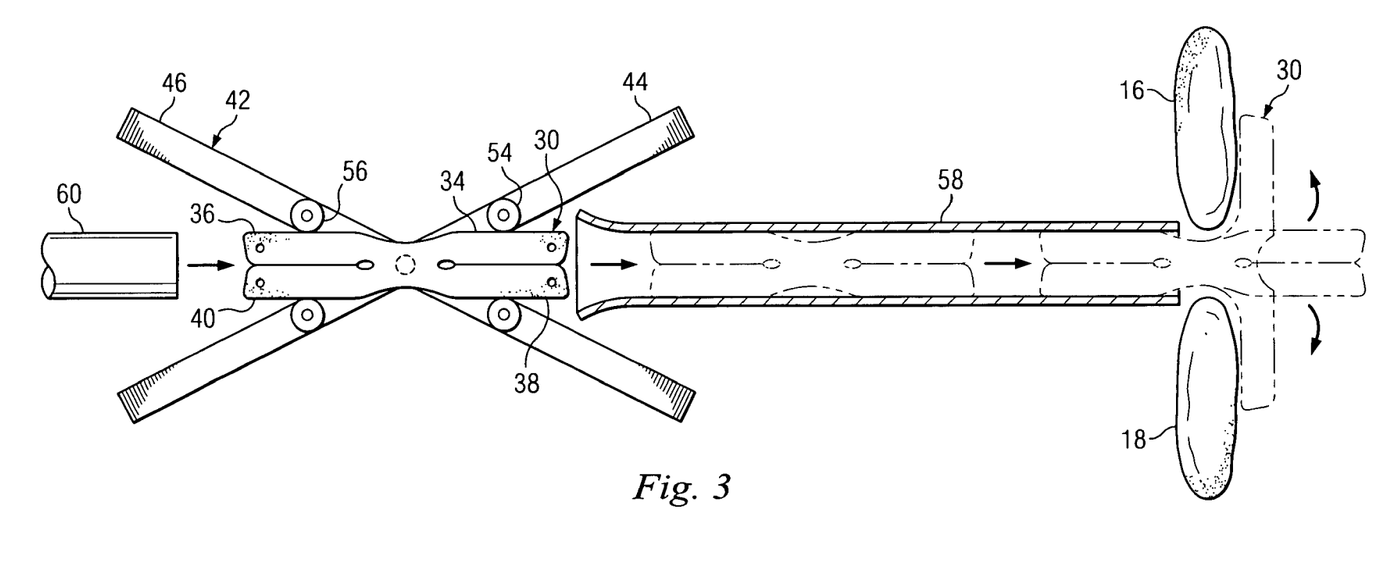
FIG. 3 is an implantation system including the instrument and spacer of FIG. 2.

Referring now to FIG. 3, the deformation instrument 42 may be used to deform the spacer 30 into a collapsed state suitable for implanting the spacer 30 into a patient in a minimally invasive way. With the deformation instrument 42 positioned as shown in FIG. 2 with the rollers 54, 56 engaged with the arms 34, 36, respectively, the supports 44, 46 are pivoted about the pivot mechanism 48. As the supports 44, 46 are moved, the rollers 54, 56 are separated, moving the spacer 30 into a collapsed state with arms 34 and 38 moved toward one another and arms 36, 40 moved toward each other. As the supports 44, 46 are moved, the rollers 54, 56 may roll along the arms 34, 36, reducing friction while collapsing the spacer 30.

A cannula 58 may be inserted into the vicinity of a patient's vertebral column and positioned adjacent to or between the spinous processes 16, 18 of a spinal joint 10. The spacer 30, now in a collapsed state, may be positioned at the opening of the cannula 58. An insertion instrument 60, such as a probe, may then be used to push the spacer 30 along the rollers 54, 56, into the cannula 58, and into the interspinous process space 20. As the spacer 30 is pushed from the cannula 58, it returns from the collapsed state to the uncollapsed state and assumes its original "X" shape with the blocking portion 32 positioned between the adjacent spinous processes 16, 18 and the unfolded arms 34, 38 extending upward and downward along one side of two spinous processes, as shown in FIG. 3. The cannula 58 is then withdrawn as the spacer 30 is ejected, and the second pair of arms 36 and 40 unfolds to extend upward and downward along the second side of the spinous processes, as shown in FIG. 3.

The surgery may be accomplished using, for example, a posterior oblique approach through a small incision in the patient's back. Prior to the implantation of the interspinous process spacer, the interspinous space may be prepared by removing soft tissue from around the spinous processes. The spinous processes may also be distracted to enlarge the space for receiving the spacer.

Figure 4:
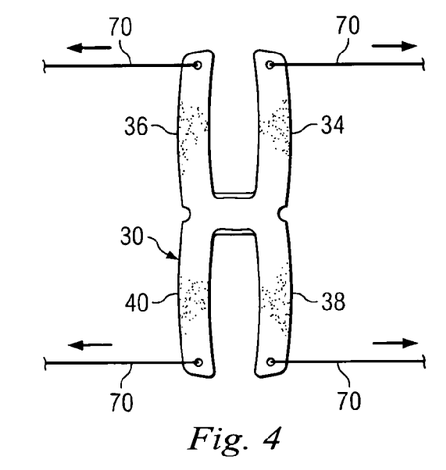
FIG. 4 is an interspinous process spacer engaged with a spacer deformation instrument according to another embodiment of the present disclosure.
Figure 5:
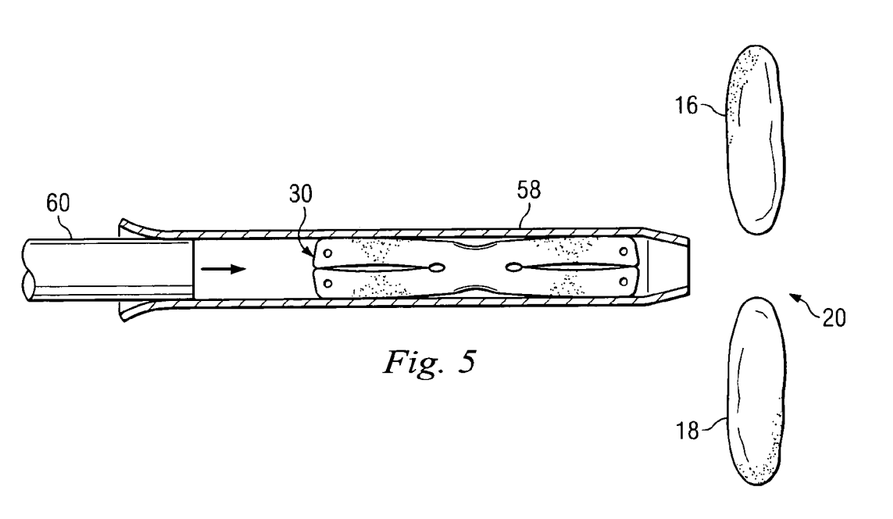
FIG. 5 is an implantation system including the instrument and spacer of FIG. 4.

Referring now to FIG. 4, the spacer 30 may be reduced to a collapsed state using an alternative embodiment of a deformation instrument. The deformation instrument may include a pulling device 70 that may include wires attached to each of the arms 34, 36, 38, 40. In use, the wires may be used to collapse the spacer 30 by pulling arms 38, 38 together and arms 36, 40 together. As shown in FIG. 5, the collapsed spacer 30 may then be introduced to cannula 58, with the wires 70 removed, and implanted between the spinous processes 16, 18 as described above.

Figure 6:
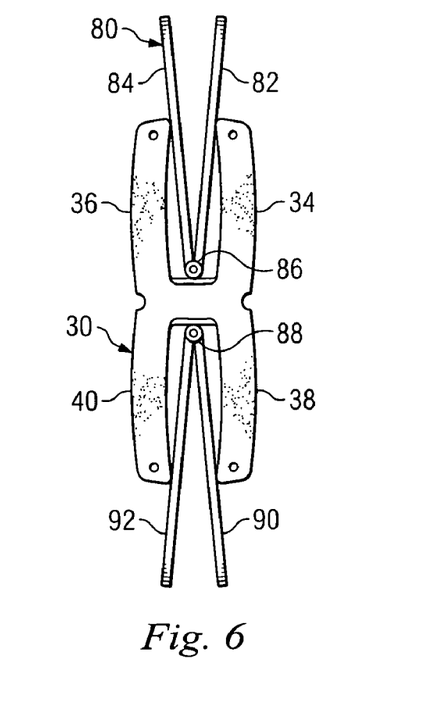
FIG. 6 is an interspinous process spacer engaged with a spacer deformation instrument according to another embodiment of the present disclosure.

Referring now to FIG. 6, a deformation instrument 80 may, alternatively, be used to reduce the spacer 30 from an uncollapsed to a collapsed state. The instrument 80 may comprise a pair of actuators or supports 82, 84 connected by a pivot mechanism 86. In use, the pivot mechanism 86 may be positioned between the arms 34, 36 of the spacer 30 with the supports 82, 84 engaged with the arms. The deformation instrument 80 may include a second pivot mechanism 88 and supports 90, 92 that are substantially similar to those described above for positioning between the arms 38, 40. The movement of the pivot mechanism 86 may be controlled or biased by a mechanical spring mechanism, a ratchet mechanism, a shape memory material, or other bias or control mechanisms known in the art.

Figure 7:
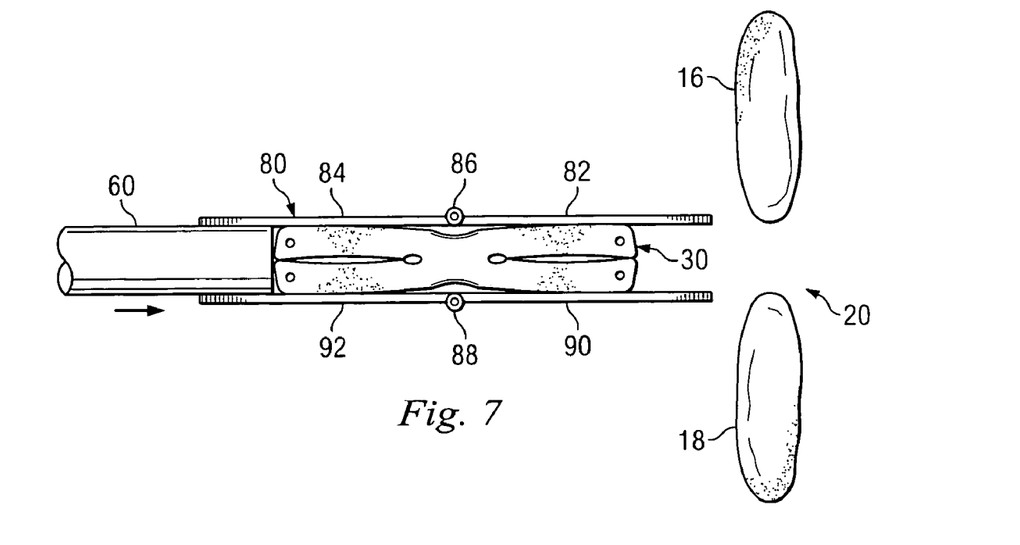
FIG. 7 is an implantation system including the instrument and spacer of FIG. 6.

With the deformation instrument 80 positioned within the spacer 30, pivot mechanism 86 may be operated to move the supports 82, 84 from a "V" shaped configuration to a straight or elongated configuration (as shown in FIG. 7). The pivot mechanism 88 and supports 90, 92 located between arms 38, 40 may operate in a similar manner to reduce the spacer 30 from an uncollapsed state to a collapsed state. The straightened supports 82, 84, 90, 92 may form a portion of a guide tube which may serve a similar function as the cannula 58 described above.

As shown in FIG. 7, with the collapsed spacer 30 positioned within the guide tube formed by the straightened supports 82, 84, 90, 92, the insertion instrument 60 may be used to push the spacer 30 through the guide tube and into the interspinous process space 20 where it is allowed to return to its uncollapsed state.

Figure 8:
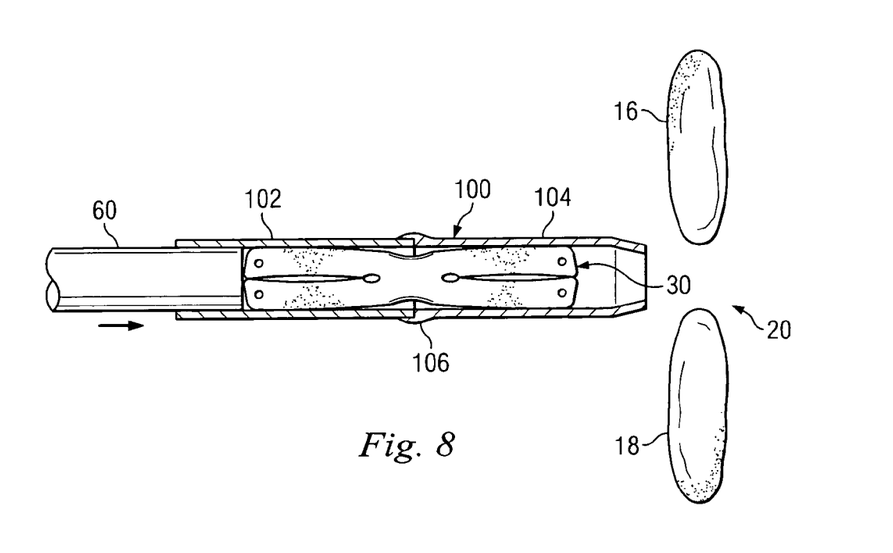
FIG. 8 is an implantation system according to another embodiment of the present disclosure.

Referring now to FIG. 8, in an alternative embodiment to cannula 58 or the guide tube created by supports 82, 84, 90, 92, a multi-part cannula 100 may include two cannula halves 102, 104. The cannula half 102 may be sized and configured to fit within a flare 106 of the cannula 104 to form a single, essentially continuous cannula. The collapsed spacer 30 may be deformed using any of the deformation instruments described above and inserted through the cannula 100 using any of the techniques described above. The multi-part cannula 100 may suitable for situations in which the arms 36, 40 are collapsed prior to collapsing the arms 34, 38. The multi-part cannula 100 allows one half of the spacer 30 to be held in a collapsed position while the opposite half of the spacer is being collapsed.

Figure 9:
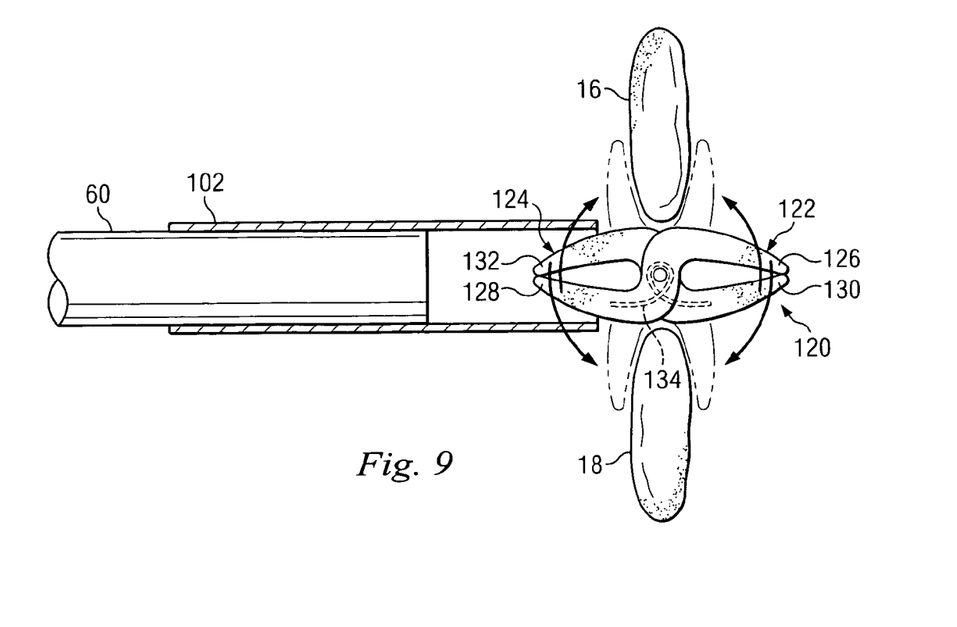
FIG. 9 is an implantation system and interspinous process spacer according to another embodiment of the present disclosure.

Referring now to FIG. 9, a spacer 120 includes a body 122 having arms 126, 128 and a body 124 having arms 130, 132. The spacer 120 may further include a spring 134 to bias the arms into an uncollapsed position. Such an embodiment may work much like a pair of scissors, with the four arms 126, 128, 130, 132 extending from a central pivot. As with scissors, the device may be converted from a generally "X"-shaped device to a generally "I"-shaped device by pivoting one pair of arms relative to the other. Such a spacer is disclosed in detail in pending U.S. patent application Ser. No. 10/851,889, entitled "Interspinous Spacer" which is incorporated herein by reference.

The spacer 120 may be collapsed using any of the deformation instruments disclosed above or any other deformation technique known in the art. In a collapsed configuration, as shown in FIG. 9, arms 132, 128 are drawn together, and arms 126, 130 are drawn together. The spacer may then be delivered to the interspinous process space 20 using any of the cannula configurations disclosed above. When the spacer 120 is ejected from the cannula, the spring 134 may bias the spacer 120 to return to its uncollapsed state.

Figure 10:
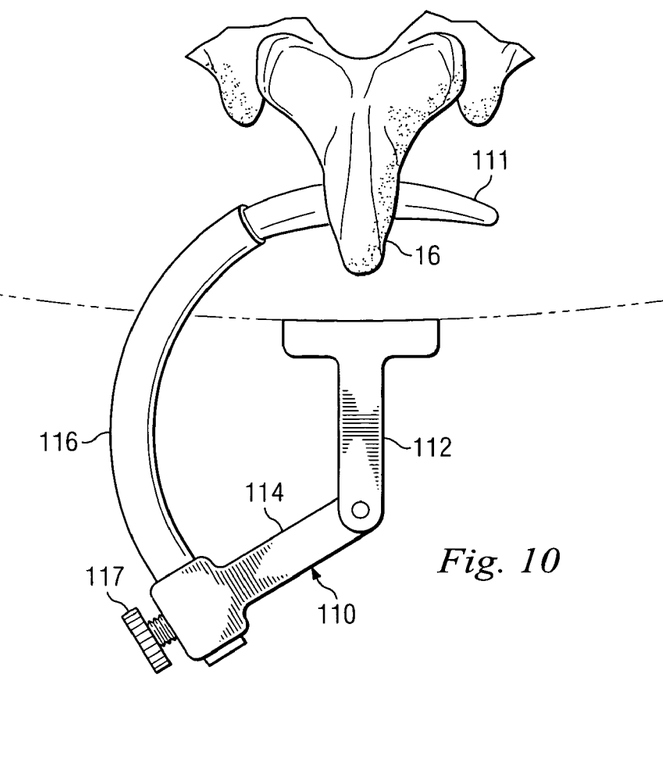
FIG. 10 is an implantation system according to another embodiment of the present disclosure.

Referring now to FIG. 10, in this embodiment, precision alignment through a minimally invasive approach may be achieved with an installation instrument 110 used to install a spacer 111 between spinous processes 16, 18. The installation instrument 110 includes a fixed member 112 which is connectable to either a fixed location on the patient's body or to an external location. A swing member 114 may have a distal end pivotally connected to the fixed member 112. A proximal end of the swing member 114 may be connected to a curved member 116. The curved member 116 may be a curved cannula capable of receiving an interspinous process spacer. Alternatively, the curved member may have a holder for attaching a spacer to a distal end of the curved member. The swing member 114 may be connected to the curved cannula 116 with a release knob 117 to allow for simplified release and locking of the curved cannula 116 to the swing member 114.

In use, the fixed member 112 may be held stable relative to the interspinous space 20. An interspinous process spacer 111 may be collapsed using one of the methods described above or any other known in the art. With the swing member 114 detached or extended away from the interspinous process space 20, the collapsed spacer may be inserted through the curved cannula 116. The swing arm 114 may then be pivoted to move the curved cannula to the interspinous process space 20. The spacer 111 may then be ejected from the curved cannula 116. The use of the installation instrument 110 may reduce the invasiveness of the spacer implantation by delivering the spacer to the interspinous space with a controlled and precise technique. Such a technique may improve efforts to preserve the surrounding soft tissue. Several features of the minimally invasive installation instrument are disclosed in pending U.S. patent application Ser. No. 10/769,569 which is incorporated herein by reference.

In this embodiment, the spacer 111 may be similar to either spacer 30 or spacer 120 but may include additional features which permit a more minimally invasive implantation using the installation instrument 110. For example, the spacer 111 may be "banana" shaped or slightly curved in the direction of insertion. The curvature of the spacer 111 may match the curvature of the curved cannula 116.

Figure 11:
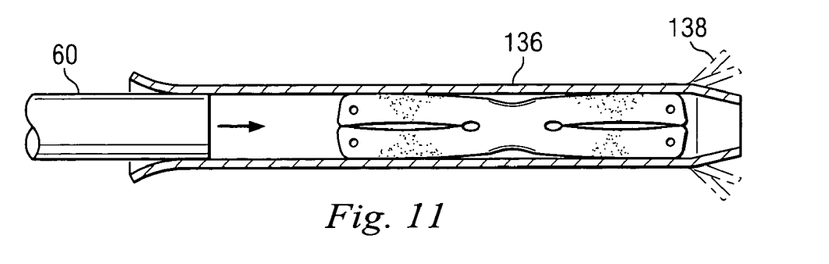
FIG. 11 is an implantation system according to another embodiment of the present disclosure.

Referring now to FIG. 11, in an alternative embodiment, a cannula 136 may have a distal end section with an opening 138 that may be enlarged to permit distraction of the adjacent spinous processes. In use, the cannula 136 may be inserted through a minimally invasive opening and positioned between the spinous processes 16, 18. Once in position, the opening 138 may be enlarged to further separate the spinous processes and provide additional space to position a spacer. The enlargement of the opening may be mechanically or thermally actuated.

Figure 12:
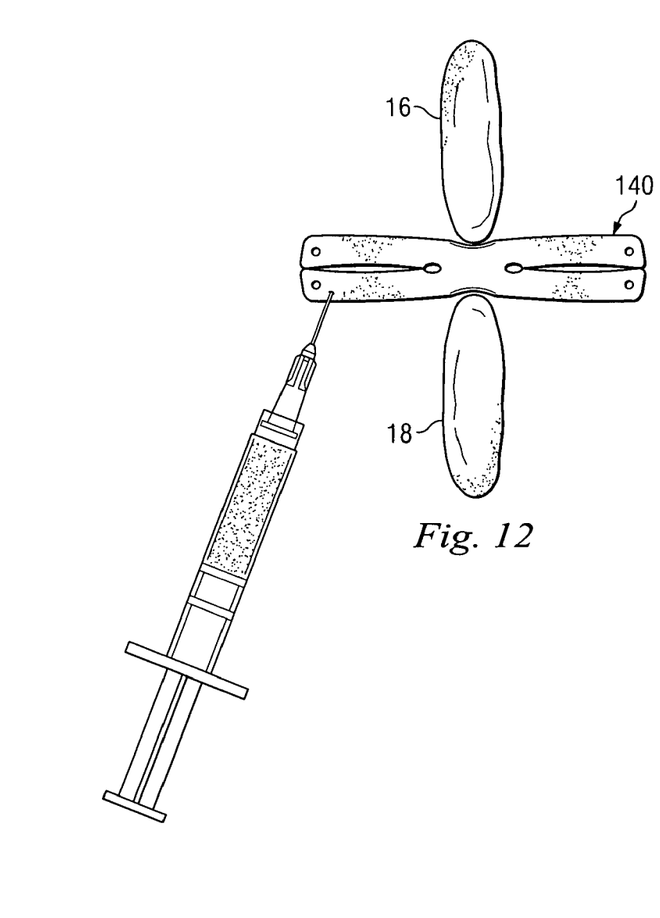
FIG. 12 is an interspinous process spacer according to another embodiment of the present disclosure.
Figure 13:
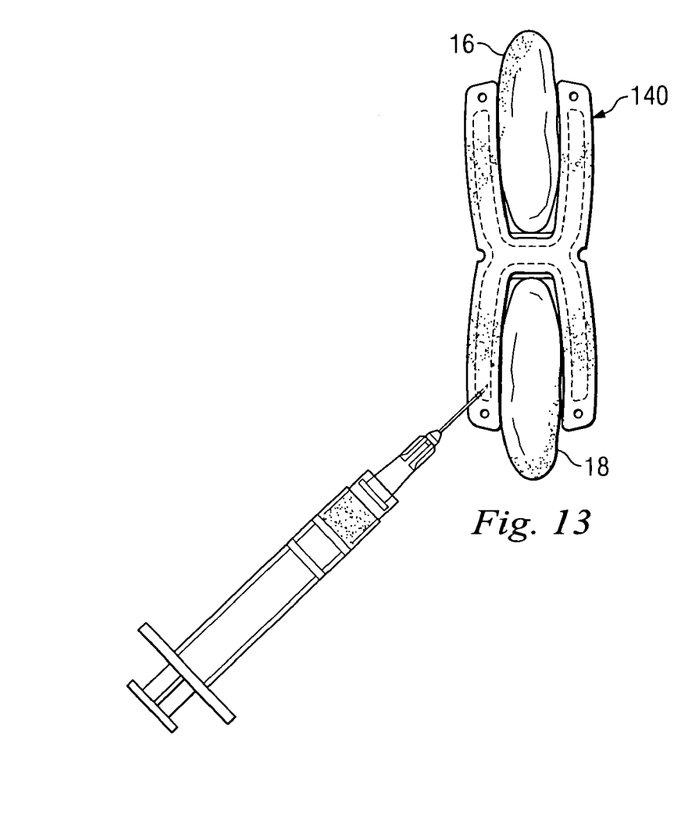
FIG. 13 is a view of the spacer of FIG. 12 after transformation to an uncollapsed state.

The deformation instruments, installation instruments, and cannula systems described above may also be used to deliver other types of interspinous process devices. For example, as shown in FIGS. 12 and 13, a fillable spacer 140 may inserted between the spinous processes 16, 18 in a collapsed and unfilled state. Once in position, the fillable spacer 140 may be injected or otherwise filled with any of a variety of filling materials to transform the spacer 140 from the collapsed state to an uncollapsed state.

Examples of injectable materials for injection into the inflatable interspinous process spacers include elastomers, hydrogels, or rigid polymers. Examples of elastomers include silicone elastomers, polyurethane elastomers, silicone-polyurethane copolymers, polyolefin rubbers, butyl rubbers, or combinations thereof. Example of hydrogels include polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), sulfonated polymers, or combinations thereof. Examples of rigid polymers include polymethylmethacrylate, silicones, polyurethanes, polyvinyl alcohol, polyamide, aromatic polyamide, polyether, polyesterliquid crystal polymer, ionomer, poly(ethylene-co-methacrylic) acid, PBT (polybutylene terephthalate), polycarbonate, or combinations Suitable materials may be natural or synthetic. The filling materials may cure or polymerize in situ. The filling materials may be transformable such that when the spacer is filled and in an uncollapsed state, the material may harden to create a rigid spacer.

Figure 14:
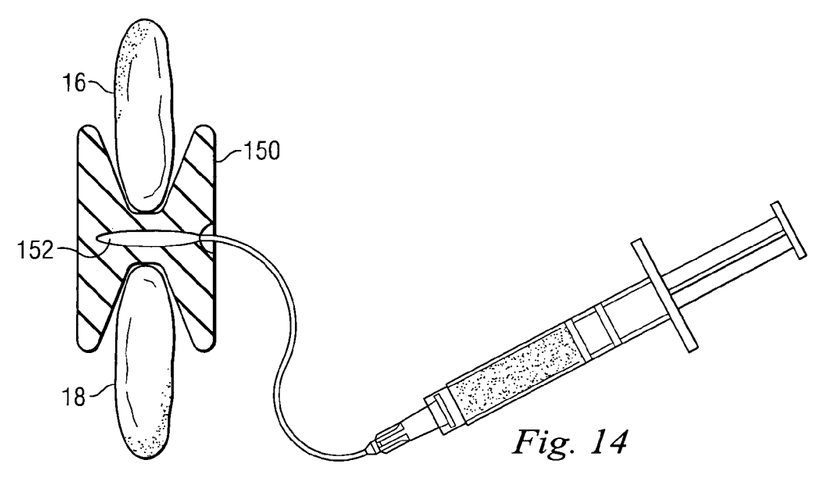
FIGS. 14-15 show an interspinous spacer according to another embodiment of the present disclosure.
Figure 15:
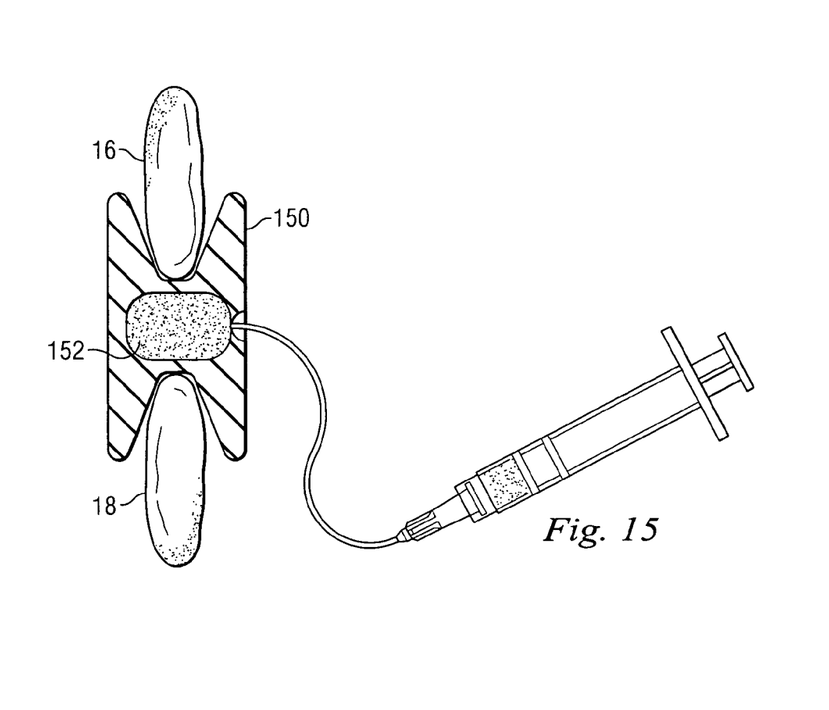

In an alternative embodiment as shown in FIG. 14, a fillable spacer 150 may include one or more inflatable chambers 152. In this example, the arms of the spacer 150 may be formed of solid elastomeric material and the blocking portion of the spacer may include the inflatable chamber 152 to allow the physician to create a customized distraction between the spinous processes. This spacer 150 may be inserted in a collapsed state, with the arm folded into a low profile package, using any of the instruments described above. When implanted the arms of the spacer 150 may unfold as shown in FIG. 14 and the chamber 152 may be subsequently filled with a material, including those filling materials described above, to distract the spinous processes to a desired level as shown in FIG. 15. The in situ curable materials may cure to a compliant or rigid mass depending upon the materials selected. Biological or pharmaceutical agents may be added to the filling material.

The arms of the spacer may be elastic or rigid and formed of any of the materials listed above. When used with rigid arms, an injectable material capable of setting or curing can lock the rigid arms into a desired position.

The partially inflatable spacer 150 may be incrementally adjustable to allow for better fit and customized distraction. Because the chambers 152 may be filled to different levels, the need to maintain large inventories of implants in a wide variety of sizes may be reduced.

The delivery of any of the spacers described above may facilitated by lubricating any of the instruments described above. Suitable lubricants may include oils, solvents, bodily fluids, fat, saline, or hydrogel coatings. For example, in FIG. 3, a lubricant may be applied to the rollers 54, 56, and to the interior shaft of the cannula 58 to reduce friction and ease the passage of the spacer 30.

In still another alternative, spinous process systems may include artificial ligaments or tethers for connecting two or more spinous processes. These ligaments may be connect to or extend through a spacer and wrap around one or both of the adjacent spinous processes to hold the spacer securely in place. Such ligaments may be elastic or non-elastic and may be made of woven or braided textiles.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A method of implanting an interspinous process spacer comprising:
   deforming an interspinous spacer having first and second pairs of resiliently deformable arms extending from a central section; the deforming comprising moving the first pair of arms toward each other from an extended configuration to a collapsed configuration;
   after the deforming, advancing the spacer in a guide tube with the first pair of arms in the collapsed configuration such that first pair of arms is constrained only by the guide tube;
   positioning the guide tube such that a distal portion thereof is disposed proximate a pair of adjacent spinous processes; and
   thereafter, pushing the spacer distally through the guide tube such that the first pair of arms and central section exits the distal portion of the guide tube; the first pair of arms exiting the guide tube prior to the central section; the first pair of arms assuming the extended configuration after the exiting such that the first pair arms resiliently move away from each other and move toward the second pair of arms, and wherein the first pair of arms are disposed on a common lateral side of the spinous processes.

2. The method of claim 1 wherein the interspinous spacer is deformed with a deformation instrument having first and second movable portions and the step of deforming further comprises pivoting the first movable portion relative to the second movable portion.

3. The method of claim 2 wherein first and second projections extend outwardly from the first and second movable portions respectively and the step of deforming further comprises engaging the first projection with one of the first pair of arms and engaging the second projection with the other of the first pair of arms.

4. The method of claim 1 wherein when the first pair of arms is moved toward each other, the first pair of arms extend in a generally lateral direction from the central section.

5. The method of claim 1 wherein the guide tube is a first guide tube, the method further comprising:
   moving the arms of the second pair of arms toward each other from the extended configuration to the collapsed configuration;
   after moving the arms of the second pair of arms, advancing the spacer in a second guide tube with the second pair of arms in the collapsed configuration such that the second pair of arms is constrained only by the second guide tube.

6. The method of claim 5 further comprising inserting the second guide tube at least partially into the first guide tube.

7. A method of implanting an interspinous process spacer comprising:
   providing an interspinous process spacer having first, second, third, and fourth arms extending from a central body; the central body having a longitudinal axis;
   the spacer having an initial state wherein the first and second arms form a first saddle for receiving a spinous process and the third and fourth arms form a second saddle; the first and second saddles facing away from each other in generally opposite directions;
   deforming the spacer to a deformed state by moving the first and third arms toward each other so that the first and third arms are oriented closer to parallel to the longitudinal axis than in the initial state and moving the second and fourth arms toward each other so that the second and fourth arms are oriented closer to parallel to the longitudinal axis than in the initial state;
   thereafter, advancing the spacer in a cannula in the deformed state such that the first and third arms are constrained only by the cannula;
   thereafter, directing the spacer from the cannula to a position between adjacent upper and lower spinous processes such that the spacer moves from its deformed state towards its initial state, with a first spinous process disposed in the first saddle and an adjacent second spinous process disposed in the second saddle;

wherein when the spacer moves from its deformed state towards its initial state, the first arm moves toward the second arm and the third arm moves toward the fourth arm.

8. The method of claim 7 wherein the spacer is deformed with a deformation instrument having first and second movable portions and the step of deforming further comprises pivoting the first movable portion relative to the second movable portion.

9. The method of claim 7 wherein when the first and third arms are moved toward each other, the first and third arms extend in a generally lateral direction from the central body.

10. The method of claim 7 wherein directing the spacer from the cannula comprises pushing the spacer from the cannula.

11. The method of claim 1 further comprising removing the spacer from the guide tube by pushing the spacer from the guide tube.

12. The method of claim 7 wherein the cannula is a first cannula and the method further comprises:

after moving the second and fourth arms towards each other, advancing the spacer in a second cannula wherein the second and fourth arms are constrained only by the second cannula.

13. The method of claim 12 further comprising inserting the first cannula at least partially into the second cannula.

\* \* \* \* \*